United States Patent
Van Dyke et al.

(10) Patent No.: US 6,544,726 B1
(45) Date of Patent: Apr. 8, 2003

(54) KVD SOLUTION FOR TRANSPLANTABLE ORGANS

(76) Inventors: Knox Van Dyke, 106 Morgan Dr., Morgantown, WV (US) 26505; Meir S. Sacks, 5446 Guarino Rd., Pittsburgh, PA (US) 15217

( * ) Notice: Subject to any disclaimer, the term of this patent is extended or adjusted under 35 U.S.C. 154(b) by 0 days.

(21) Appl. No.: 09/565,404

(22) Filed: May 5, 2000

Related U.S. Application Data

(60) Provisional application No. 60/132,633, filed on May 5, 1999.

(51) Int. Cl.$^7$ .................................................. A01N 1/00
(52) U.S. Cl. ........................................................ 435/1.2
(58) Field of Search ................................... 435/1.2, 1.1

(56) References Cited

U.S. PATENT DOCUMENTS

| | | | |
|---|---|---|---|
| 4,798,824 A | | 1/1989 | Belzer et al. |
| 4,873,230 A | | 10/1989 | Belzer et al. |
| 4,879,283 A | | 11/1989 | Belzer et al. |
| 5,834,178 A | | 11/1998 | Churchill et al. |
| 5,885,842 A | * | 3/1999 | Lai |

OTHER PUBLICATIONS

Marubayashi et al., Present status and future for organ preservation, Hiroshima Igaku, 1999, vol. 52, No. 3, pp. 211–217.*

W. Ko Et Al., "*Compositional analysis of a Modified Unversity of Wisconsin Solution for Extenede Myocardial Preservation*", Myocardial Protection, Cardiopulmonary Bypass, and Other Problems in Cardiovascular Surgery, Circulation, Supplement II (Nov. 1992) pp. II–326–II–332, vol. 86, No. 5.

M.P. Nutt, Ba Et Al., "*Assessment of Function, Perfusion, Metabolism, and Histology in Hearts Preserved with University of Wisconsin Solution*", Circulation, Supplement II, (Nov. 1992) pp. II–333–II–338, vol. 86, No. 5.

A. G. Upadhya Et Al., "*Evidence of a Role for Matrix Metalloproteinases in Cold Preservation Injury of the Liver in Humans and in the Rat*", Hepatology (1997), vol. 20, No. 4.

G. A. Upadhya and S. M. Strasberg, "*Glutathione, Lactobionate, and Histidine: Cryptic Inhibitors of Matrix Metalloproteinases Contained in University of Wisconsin and Histidine/Tryptophan/Ketoglutarate Liver Preservation Solutions*", Hepatology (May 2000) pp. 1115–1121, vol. 31, No. 5.

* cited by examiner

*Primary Examiner*—Sandra E. Saucier
(74) *Attorney, Agent, or Firm*—Alan G. Towner, Esq.; Pietragallo, Bosick & Gordon

(57) ABSTRACT

The present invention is directed to a composition and method of preserving organs comprising exposing said organs to a preservation solution that includes at least an inhibitor or quencher of peroxynitrite. In its most easily formulated embodiment the present invention is a modified Wisconsin solution which includes the inhibitor or quencher as described herein.

6 Claims, No Drawings

KVD SOLUTION FOR TRANSPLANTABLE ORGANS

This application claims the benefit of Provisional application Ser. No. 60/132,633, filed May 5, 1999.

BACKGROUND OF THE INVENTION

1. Field of the Invention

This invention relates to the field of preservation of biological materials for transplantation, and more particularly to compositions and methods for the resurrection and preservation of organs, tissues and cells from mammals.

2. Background and Description of the Related Art

Organ transplantation has become a relatively common procedure. Major solid organs that are routinely transplanted include the liver, kidney, heart, pancreas, lung and small bowel. The success of organ transplantation is due, in part, to the development of preservation solutions which allow for the shipment of cadaveric organs to transplant centers around the country. Cadavers are the main source of organs for transplantation. To optimally utilize all available organs it is necessary to be able to preserve viability while the organ is being shipped to the most suitable recipient. Suitability is generally based upon histocompatability matching of six-antigen matches between the donor and recipient.

When transplant organs are removed from the donor's body, the blood supply is interrupted. This action also interrupts the source of the organ's supply of oxygen, carbon dioxide, nitric oxide and nutrition, as well as the liquids that contain the necessary salts to create the correct osmotic pressure for a healthy osmotic environment for the tissue. Organ preservation methods are directed at minimizing the effects of interrupting the blood supply.

There are two main methods for clinical organ preservation. Simple cold storage is the most common and involves flushing the blood out of the organ and infusing it with a cold preservation solution. The second method is machine perfusion and involves continuous perfusion of the organ with a perfusate maintained at a temperature of 4° C. to 8° C. Perfusion is done at low pressure and usually with the pulsatile flow of about 0.6 to 10 ml/min/g of tissue. An advantage of perfusion is that end products from metabolism can be removed and that oxygen and other substrates can be delivered to the organ. Thus, energy requiring reactions that continue, even at hypothermia, can be supplied with a constant source of ATP derived from mitochondrial oxidative phosphorylation. Perfusion, therefore, provides longer preservation of organs than cold storage, and in general does a better job of preserving the quality of organs for short periods of time.

In 1967, Belzer et al. ("Belzer") developed the method of continuous perfusion for preserving dog kidney for three days. The initial attempts at perfusion used plasma as the perfusate, but vascular injury resulted from the cold-induced precipitation of lipoproteins in the glomerular vessels. Belzer was able to overcome this limitation by first freezing the plasma and then filtering the precipitated lipoproteins. This led to the development of cryoprecipitated plasma (CPP) as the first successful perfusion fluid for hypothermic storage of kidneys. The solution worked well for a three day preservation of dog kidney but was unsuccessful for longer periods. Additionally, the CPP solution was unstable and needed to be prepared fresh for each use. Subsequently, a plasma based perfusion solution was developed that removed the lipid components by mixing silica gel with the plasma. The silica gel fraction of this plasma-based perfusion solution was as effective as CPP and was also shelf stable. Others attempted to develop perfusates based on saline mixed with human serum albumin as a colloid. All of the perfusates were about equally effective for kidney preservation and have been used clinically.

Belzer's interest in improving machine perfusion of kidneys to obtain longer term perfusion (5–7 days), led to the development of the composition commonly known as the University of Wisconsin Solution (Table 1). The original Wisconsin Organ Preservation Solution has allowed preservation of a variety of organs for transplantation including heart, liver, kidney and lungs, (Transplant Proceedings, 20-Supplement 1, p. 945, 1988, incorporated herein by reference as if set forth in its entirety herein).

TABLE 1

| |
|---|
| 5% hydroxyethyl starch having a molecular weight of from about 200,000 to about 300,000 and a degree of substitution of from 0.4 to 0.7. |
| 25 mM $KH_2PO_4$ |
| 3 mM glutathione |
| 5 mM adenosine |
| A0 mM glucose |
| 10 mM HEPES Buffer (Sigma Chemical Company) |
| 5 mM magnesium gluconate |
| 1.5 mM $CaCl_2$ |
| 105 mM sodium gluconate |
| 200,000 units of penicillin |
| 40 units insulin |
| 16 mg Dexamethasone |
| 12 mg Phenol Red |
| pH 7.4–7.5 |

This solution has found widespread clinical application for the preservation of the major intra-abdominal organs, and is the subject of three issued U.S. Patents (U.S. Pat. No. 4,798,824; U.S. Pat. No. 4,873,230; U.S. Pat. No. 4,879,283), all of which are incorporated herein by reference as if set forth in their entirety herein.

Even with the advent of improved techniques and organ preservation solutions, over the years, reperfusion injury (RI) still occurs. This injury is most commonly recognized as oxidative damage to the organ. For example, Starzl et al. reported substantial deterioration of liver after 20 hours (Transplantation, 51, pp. 1000–04, 1991). Yamaguchi et al. has observed that highly toxic oxidizing substances, such as peroxynitrite and hypochlorite, can be formed as part of RI (Hepatology, 29, pp. 777–84, 1999). Furthermore, Bahr et al. has reported that damage to the liver can cause net accumulation of extra cellular matrix and matrix degradation by a family of zinc-dependent metalloproteinases, including collagenases, gelatinases, stromolysins, MT-MMP's (Hepatology 29, pp. 839–45, 1999).

Modified forms of the University of Wisconsin Solution have been shown to have certain benefits for prolonged cardiac preservation. Nutt et al. compared the effects of twenty-four hour cold storage with perfusion preservation using a modified University of Wisconsin Solution. They found that perfusion with the modified solution provided function that was comparable of that of the cold storage control. (Circulation 1992; 86 [Suppl II]: II-333–II-338, herein incorporated by reference).

It was widely thought that one mechanism of RI was xanthine oxidase activation and its reaction with hypoxanthine, xanthine, or other substrates which can produce a superoxide anion from molecular oxygen. However, the toxicity of superoxide anion itself was never clear. It is known that superoxide anion reacting with nitric oxide can produce a highly toxic substance known as peroxynitrite anion. If the peroxynitrite anion is in the presence of a proton (H+), peroxynitrous acid is produced. Peroxynitrous acid can attack almost any biochemical entity. Peroxynitrite itself can cause DNA to be nicked or split resulting in a major insult to the cell and can eventually lead to apoptosis.

Churchill et al. have recently described chemical solutions that are suitable for flushing the blood from a donor organ prior to transplantation in U.S. Pat. No. 5,834,178 herein incorporated by reference in its entirety.

In addition to interrupting the blood supply in the organ prior to transplant into the recipient, cells of the donor are trapped in situ and provide challenges of their own. Regardless of how many loose cells can be washed from the organ prior to transplant with perfusion, it is not possible to clear all of the host cells, i.e., lymphocytes, monocytes, macrophages or neutrophils, of the donor from the organ to be transplanted. The host cells represent an antigenic challenge to the recipient in addition to the antigenic load the new organ itself represents. These cells that remain in the donor organ can be activated to produce substances toxic to the recipient.

A crucial mechanism which is activated during the transplantation of an organ is known as nuclear factor (Nf) kappa b, which is known to be manifested as a gene stimulation mechanism in the cells that remain in the donor organ. Once this mechanism is initiated, many genes of the immuno-inflammatory system that have a Nf kappa b gene control mechanism in their promoter region are activated. This leads to an antigenic response that may ultimately result in rejection of the transplanted organ.

SUMMARY OF THE INVENTION

In summary, the present invention provides compositions for the preservation of biological materials which compositions are formulated to reduce or eliminate reperfusion injury and/or to decrease antigenic response in a recipient upon transplantation.

An improved Wisconsin solution is disclosed wherein the improvement comprises a therapeutically effective concentration of a biological equivalent of uric acid. The biological equivalent is a precursor of uric acid selected from the group consisting of DNA, RNA, nucleotides of DNA, nucleotides of RNA, nucleosides of DNA, free bases of DNA, free bases of RNA, hypoxanthine, and xanthine. The precursor of uric acid is hypoxanthine. The biological equivalent of uric acid is a solubilized equivalent of uric acid. The composition may further include an agent which inhibits induction of Nf kappa B and may further include a gluccocorticoid, a non-gluccocorticoid lazaroid, a tetracyclin equivalent, and pentoxyphyline. The composition may further include a therapeutically effective concentration of an inhibitor of NO synthase. The inhibitor of NO synthase is selected from the group consisting of L-NAME, L-arginine, ascorbic acid, ascorbate, and tocopherols. The biological equivalent of uric acid is a sugar based equivalent. The sugar based equivalent is uric acid—osine.

Further, a composition is provided for the preservation of tissue comprising: an inhibitor of peroxynitrite; an inhibitor of Nf kappa B induction; and an inhibitor of nitric oxide synthase. The inhibitor of peroxynitrite is selected from the group consisting of DNA, RNA, nucleotides of DNA, nucleotides of RNA, nucleosides of DNA, free bases of DNA, free bases of RNA, hypoxanthine, and xanthine. The inhibitor of peroxynitrite is selected from the group consisting of biological equivalents of uric acid, polyphenolic compounds, and spin traps. The biological equivalent of uric acid is hypoxanthine. The composition may further include an inhibitor of homocysteine formation selected from the group consisting of Vitamin $B_6$ and folic acid.

DESCRIPTION OF THE PREFERRED EMBODIMENTS

In accordance with the present invention, a composition is provided for the resurrection and preservation of transplantable organs that reduces or eliminates reperfusion injury, and increases organ viability for extended periods of time. The composition also reduces antigenic response in a recipient following transplantation. The composition preferably contains a significant amount of a water soluble substance to inhibit Nf kappa b. The solution may also contain a large amount of non-assimilated polymer which has the ability to bind fat soluble substances that themselves might not be readily soluble. The composition of the present invention may also contain L-glycine, and/or an equivalent nitric oxide (NO) donor, and/or a substrate for NO. Soluble xanthine oxidase inhibitor may also be provided.

Additional substances may be included which: maintain a desired pH; inhibit peroxynitrite; serve as a source of magnesium; inhibit nitric oxide synthase; provide anti-bacterial action against gram positive and gram negative bacteria; provide potassium and phosphate to balance the osmolarity of the solution; react intracellularly with superoxide anion to form hydrogen peroxide; serve as a backup energy source; provide essential amino acids; allow glucose to penetrate the cells; and act as a pH indicator. Further details on substances to include in the solution of the instant invention may be found in the latest edition of *Remington's Pharmaceutical Sciences* (Maack Publishing Co., Easton, Pa.) hereby incorporated herein by reference in its entirety.

Perfusion is used in the present invention in its broadest context to include not only mechanical machine perfusion, but also all means of flushing, washing, bathing, cleaning, diffusing or exposing transplantable biological materials to the compositions described herein. The perfusion may be pulsatile, continuous or irregular in nature.

As used herein, transplantable biological materials include, but are not limited to, any mammalian organ, tissue, structure, cell, or membrane, regardless of whether the source is from cadaveric origin, human origin, laboratory origin, or mechanical manufacture. Suitable organs on which the solutions of this invention may be used include, for example, heart, liver, kidney, lungs, pancreas, small bowel.

In accordance with the present invention of using a solution to resurrect or preserve transplantable organs, compositions are provided to alleviate RI and the concomitant antigenic reactions that result from transplantation. The present invention is directed towards preventing such toxic events by implementing a defensive strategy wherein the toxic substance is either blocked prior to its manufacture, or destroyed before it attacks any biological entity. The compositions utilize a variety of components to address specific aspects of reperfusion injury and antigenic response.

To be appropriate and effective, a perfusion solution should have a composition that: (1) minimizes hypothermic-induced cell swelling; (2) prevents intracellular acidosis; (3) prevents the expansion of extra-cellular space during the flush-out period; (4) prevents damage from oxygen-free radicals, i.e., reperfusion injury; (5) provides substrates for regenerating high energy phosphate compounds during reperfusion; (6) inhibits nuclear factor (Nf) kappa-b to prevent gene-activation of the host cells that remain in a donor organ; and (7) is stable and safe to work with.

It is contemplated that substitutes and/or additions to the University of Wisconsin solution can be made that facilitate a reduction in RI and reduce antigenic response. For example, the addition of dexamethasone phosphate in a high dose can be used to prevent Nf kappa b activation of inflammatory mediators, such as tumor necrosis factor (TNF), interleukins, 1, 6, 8 (IL-1, IL-6, IL-8) and NO synthase, as well as adhesion factors which are dependent on the gene activating factor.

Since some of the toxic substances are composed of nitric oxide and superoxide anion, their respective production can be blocked via the inhibition of NO synthase or NADPH oxidase or xanthine oxidase, or through the activation of any of these enzymes. Substances that can either intercept nitric oxide and/or superoxide anion or react with peroxynitrite would prevent damage from occurring.

The present invention contemplates the use of uric acid and its biological equivalents and/or precursors as a useful agent to inhibit or destroy peroxynitrite and hypochlorite, along with a metalloproteinase-col3 inhibitor. The use of biological equivalents of uric acid as peroxynitrite inhibitors or quenchers is described for example in commonly owned U.S. patent application Ser. No. 09/127,184, the disclosure of which is incorporated herein by reference thereto as if set forth in its entirety herein. Preferably, the uric acid precursors are selected from the group of DNA nucleotides, RNA nucleotides, nucleosides of DNA, free bases of DNA, free bases of RNA, hypoxanthine, and xanthine. It is most preferable to utilize hypoxanthine. Further, a caspase inhibitor could be included in the composition.

A water soluble spin label, such as TEMPO or 4-hydroxyTEMPO, is suggested due to its properties as a recyclable superoxide dismutase mimic, to react with superoxide and convert it into hydrogen peroxide.

In addition, an inhibitor/binder of, or reactant with, nitric oxide (NO) can also be utilized to lower the amount of nitric oxide present so peroxynitrite cannot be formed. It is contemplated that ascorbic acid, or polyphenols (e.g. those isolated from green tea), and N-acetyl cysteine could be used as inhibitor/binders of NO. Ascorbic acid and polyphenols are known to destroy peroxynitrite, and N-acetyl cysteine is a superior producer of L-glutathione.

Adenine and ribose are contemplated as replacements for adenosine. Due to its much longer half-life, oxipurinol is contemplated as a replacement for allopurinol.

In addition, sulfinated starch can be replaced by hydroxyethyl starch. Nutt et al. has shown that lactobidnate is satisfactorily replaced by gluconate in heart transplants when used at 4° C., and, according to Ko et al., chloride could also replace lactobionate, (Circulation 1992; 86 [Suppl II]: II-326–II-332, herein incorporated by reference).

The following example illustrates the concepts of the present invention, but in no way are meant as a limitation hereto.

EXAMPLE

Example of KVD Solution[1]

| Example of KVD Solution[1] | |
| --- | --- |
| Dexamethasone phosphate | 100–500 mg/liter |
| Beta Cyclodextrin hydrate (MW 1135) | 50 g/liter |
| N-acetylcystein | 10–100 mm |
| Adenosine monophosphate | 10 mm |
| Potassium salt of polygalacturonic acid | 100 mm |
| Allopurinol | 1 mm |
| D glucose | 10 mm |
| Calcium Chloride hexahydrate | 1 mm |
| Sodium urate solution + 7 mg % L-arginine | |
| Magnesium chloride | 5 mm |
| Ng monomethyl L-arginine (L-Name) | 200 mg % |
| Salt | 500,000 units/liter |
| Potassium dihydrogen phosphate | 25 mm |
| Polyphenolic substances[2] | |
| 4 hydroxy tempo | 10 mm |
| Creatine monohydrate | 5 g/liter |
| Essential amino acids[3] | 1–10 mm |
| Insulin | 50 units/liter |
| Phenol Red | 12 mg |

[1]pH of Solution is adjusted to 7.4 with sodium hydroxide or hydrochloric acid
[2]extracted from green tea
[3]histidine, isoleucine, leucine, lysine, methionine, phenylalamine, threonine, tryptophan, and valine It will be appreciated by those skilled in the art that the actual preferred amounts of the ingredients in the specific compositions will vary according to the specific compound ratio utilized, the particular compositions formulated, and the mode of application. Concentrations for a specific circumstance can be determined using conventional considerations, e.g., by comparisons of the differential activities of the active compounds of this invention with known agents by means of an appropriate conventional pharmacological protocol and extrapolation of the dosages based on the results thereof as is known in the art.

The solution can be used at all temperatures ranging from 0° C. to normal body temperature, 37° C., more preferably the solution is used in a temperature range from 4° C. to 8° C.

It will be understood by those skilled in the art that all components in the compositions described herein are included in amounts effective to fulfill their described purpose for inclusion. For example, antioxidants are included in an amount effective to inhibit oxygen-derived free radicals; peroxynitrite inhibitors are present in an amount effective to inhibit the formation of peroxynitrite.

The individual components of the present invention are all non-toxic and have been found to be stable during storage. While some of the components of the present invention are similar to those of other known preservation solutions, it has been found that the addition of certain components described herein can alleviate reperfusion injury and/or reduce the antigenic effect of transplantation in the recipient.

The compositions of the present invention are based on a balanced isotonic solution which includes certain electrolytes in physiologically acceptable amounts. Osmolarity of the solutions can be controlled using sodium, potassium, calcium and magnesium ions, as well as glucose and/or sodium bicarbonate.

While the foregoing has been set forth in considerable detail, components of the solution are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concepts described herein.

What is claimed is:

1. An improved University of Wisconsin Solution the improvement comprising further adding to the University of Wisconsin Solution at least one of the following ingredients, hypoxanthine, xanthine or sodium urate.

2. The solution of claim 1, wherein the added ingredient is hypoxanthine.

3. The solution of claim 1, further including an agent which inhibits induction of Nf kappa B.

4. The solution of claim 1, further including a glucocorticoid, a non-glucocorticoid lazaroid, tetracycline and pentoxyphyline.

5. The solution of claim 1, further including a therapeutically effective concentration of an inhibitor of NO synthase.

6. The solution of claim 5, wherein said inhibitor of NO synthase is selected from the group consisting of L-NAME, L-arginine, ascorbic acid, ascorbate, and tocopherols.

* * * * *